United States Patent [19]

Elliott et al.

[11] Patent Number: 4,713,392
[45] Date of Patent: Dec. 15, 1987

[54] PESTICIDES

[75] Inventors: Michael Elliott, Stevenage; Norman F. Janes, Luton; Bhupinder P. S. Khambay, Harrow Weald, all of England

[73] Assignee: National Research Development Corporation, England

[21] Appl. No.: 732,642

[22] Filed: May 10, 1985

[30] Foreign Application Priority Data

May 16, 1984 [GB] United Kingdom ............... 8412480

[51] Int. Cl.⁴ ............... A61K 31/275; C07C 49/657
[52] U.S. Cl. ............... 514/464; 568/329; 568/330; 549/438; 558/404; 514/682; 514/683; 514/684; 514/520
[58] Field of Search ............... 71/123; 560/102; 568/329, 330; 549/438; 514/682, 683, 684, 520, 464; 558/404

[56] References Cited

U.S. PATENT DOCUMENTS

| 3,666,789 | 5/1972 | Itoya et al. | 560/102 |
|---|---|---|---|
| 3,997,586 | 12/1976 | Martel et al. | 560/102 |
| 4,206,230 | 1/1980 | Paul | 568/329 |
| 4,283,414 | 8/1981 | Harvey et al. | 560/102 |
| 4,360,690 | 11/1982 | Fuchs et al. | 560/102 |
| 4,390,715 | 6/1983 | Holan et al. | 560/102 |
| 4,418,202 | 11/1983 | Fayter et al. | 560/102 |
| 4,540,710 | 9/1985 | Holan et al. | 560/102 |

FOREIGN PATENT DOCUMENTS 1413491 11/1975 United Kingdom ............... 71/123

Primary Examiner—James H. Reamer
Attorney, Agent, or Firm—Jacobs & Jacobs

[57] ABSTRACT

A compound of formula II $$R_A CH_2 COCHD R_b$$

in which formula:

$R_A$ represents a group $ArCR_1R_2$— in which Ar represents a phenyl or naphthyl group optionally substituted by one or more halogen, alkoxy, haloalkoxy, methylenedioxy or $C_1$-$C_6$ alkyl or haloalkyl groups;

$R_1$ and $R_2$ together with the carbon to which they are attached jointly represent a $C_3$-$C_6$ cycloalkyl group optionally substituted by one or more halogen atoms or $C_1$-$C_6$ cycloalkyl groups and $R_B$ represents the residue of an alcohol $R_B$CHDOH in which D is hydrogen or cyano and of which the [IR, cis]2,2-dimethyl-3-(2,2-dibromovinyl)cyclopropane carboxylic ester is signficantly insecticidal.

8 Claims, No Drawings

PESTICIDES

This invention relates to pesticides and in particular to pesticidal compounds, the preparation of such compounds, intermediates for use in their preparation, compositions containing such compounds and the use of such compounds and compositions to control pests.

Accordingly the present invention comprises a compound of formula I $$R_A CH_2 COCHDR_B \qquad I$$

in which formula;

$R_A$ represents a group $ArCR_1R_2-$ in which Ar represents a phenyl or naphthyl group optionally substituted by one or more halogen, alkoxy, haloalkoxy, methylenedioxy or $C_1-C_6$ alkyl or haloalkyl groups;

$R_1$ and $R_2$ together with the carbon to which they are attached jointly represents a $C_3-C_6$ cycloalkyl group optionally substituted by one or more halogen atoms or $C_1-C_6$ alkyl groups and $R_B$ represents the residue of an alcohol $R_B CHDOH$ in which D is hydrogen or cyano and of which the [IR, cis] 2,2-dimethyl-3-(2,2-dibromovinyl)cyclopropane carboxylic ester is significantly insecticidal.

Ar is typically substituted phenyl and substitution is usually at the 3-(meta) and/or 4-(para)-position by fluorine, bromine, chlorine, a $C_1-C_6$ alkyl group e.g. methyl or tertbutyl, a $C_1-C_6$ alkoxy group e.g. methoxy, ethoxy, a halomethoxy or haloethoxy group, which may comprise one or more halogens, e.g. $OCF_3, OCF_2H$ or halomethyl or haloethyl group e.g. $CF_3$. Ar generally carries no more than two substituents, and typically only one.

The substituents $R_1$ and $R_2$, together with the carbon bearing them, typically represent a substituted or unsubstituted cyclopropyl group which, when substituted, preferably carries halogen and especially fluorine as in 2,2-difluorocyclopropyl.

When the compound of formula I is chiral (as in the immediately foregoing case) it can of course exist in different stereoisomeric forms. Both mixtures of stereoisomers and single stereoisomers are included within the scope of the present invention.

$R_B CHD$ may represent the residue of any of the alcohols of formula $R_B CHDOH$ claimed or described in the specification for UK Patent No. 1413491 which give rise to significant insecticidal activity when esterified with [IR, cis]-2,2-dimethyl-3-(2,2-dibromovinyl)carboxylic acid. Potency towards houseflies is usually at least 5 relative to bioresmethrin = 100 and may be 10 or more.

Typically $R_B CHD$ represents the residue of an alcohol $R_B CHDOH$ which is 3-phenoxybenzyl, 4-phenoxybenzyl, α-cyano-3-phenoxybenzyl, 4-fluoro-3-phenoxybenzyl, α-cyano-4-fluoro-3-phenoxybenzyl, 5-benzyl-3-furylmethyl, 3-benzylbenzyl, 4-benzylbenzyl, 3-phenyl-2-methylbenzyl, 3-phenoxy-2-chlorobenzyl or 3-benzoylbenzyl alcohol.

Compounds of formula I may be produced in accordance with a further aspect of the present invention by reaction of an acid halide of formula $R_A CH_2 COX$, in which X represents halogen e.g. chlorine with a reagent of formula $R_B CHDM$, in which M represents a species comprises a metal, e.g. as in the Grignard reagent $R_B CHDMgY$ in which Y repesents halogen, e.g. bromine.

In accordance with a further aspect of the present invention, a compound of formula I is produced by oxidation of an alcohol of formula $R_A CH_2 CHOHCHDR_B$, prepared, for example, by reaction of an aldehyde of formula $R_A CH_2 CHO$ with a Grignard reagent of formula $R_B CHDMgY$, in which Y represents halogen, e.g. bromine. Oxidation of the alcohol is suitably effected by an appropriate oxidising agent such as pyridinium chlorochromate or dichromate in a good solvent such as dichloromethane or chromium trioxide in acetone.

The present invention also includes within its scope intermediates of formula $R_A CH_2 COX$ and $R_A CH_2 CHOHCHDR_B$.

In accordance with a further aspect of the present invention, one or more of the pesticidal compounds of formula I is formulated with an inert carrier or diluent to give a pesticidal composition.

Compositions may be in the form of dusts, granular solids, wettable powders, mosquito coils or other solid preparations or as emulsions, emulsifiable concentrates, sprays or aerosols or other liquiod preparations after the addition of the appropriate solvents, diluents and surface-active agents.

The pesticidal compositions of the invention will normally contain from 0.001 to 25% by weight of the compound of formula I but the compositions can contain higher concentrations of active ingredient of formula I e.g. up to 95% for compositions to be sold as concentrates for dilution before use by the ultimate user.

The compositions of the invention can include diluents such as hydrocarbon oils, e.g. xylene or other petroleum fractions, water, anionic, cationic or non-ionic surface-active agents, anti-oxidants or other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or other types and the composition may also include synergists of the type known to be capable of synergising the activity of natural pyrethrin and pyrethroid-like insecticides. Synergists of this type include piperonyl butoxide, tropital, sesamex and propyl prop-2-ynyl phenyl-phosphonate.

Compounds of formula I can be used to control pest infestation in the domestic, horticultural or agricultural or medical, including veterinary, areas.

The compounds or compositions of the invention can be used to combat pest infestation by treating pests or surfaces of environments susceptible to pest infestation with effective amounts of the active compounds of formula I or of compositions containing them. For example, they may be used in a domestic environment for spraying rooms to combat infestation with houseflies or other insects, they can be used for treatment of stored crops or cereals to combat infestation by insects or other pests, they can be used to spray growing crops, e.g. cotton or rice to combat infestation by common pests and they can be used in a medical or veterinary field, e.g. as a cattle spray to prevent or treat infestation by insects or other pests.

The compounds may also find application in the control of virus acquisition by and/or transmission in plants particularly when mediated by aphids such as *Myzus persicae*, the peach-potato aphid.

The compounds are additionally of interest for the control of pests such as the following:

from the class of the Isopoda, for example *Oniscus asellus, Armadillidium vulgare* and *Porcellio scaber*;

from the class of the Diplopoda, for example *Blaniulus guttulatus*;

from the class of the Chilopoda, for example *Geophilus carpophagus* and *Scutigera* spec;

from the class of Symphyla, for example *Scutigerella immaculata*;

from the order of the Thysanura, for example *Lepisma saccharina*;

from the order of the Collembola, for example *Onychiurus armatus*;

from the order of the Orthoptera, for example *Blatta orientalis, Periplaneta americana, Leucophaea mardarae, Blattella germanica, Acheta domesticus,* Cryllotalpa spp., *Locusta migratoria migratorioides, Melanoplus differentialis* and *Schistocerca gregaria*;

from the order of the Dermaptera, for example *Forficula auricularia*;

from the order of the Isoptera, for example Reticulitermes spp;

from the order of the Anoplura, for example *Phylloxera vastatrix*, Pemphigus spp., *Pediculus humanus corporis*, Haematopinus spp. and Linognathus spp;

from the order of the Mallophaga, for example Trichodectes spp. and Demalinea spp;

from the order of the Thysanoptera, for example *Hercinothrips fermoralis* and *Thrips tabaci*;

from the order of the Heteroptera, for example Eurygaster spp., *Dysdercus intermedius, Piesma quadrata, Cimex lectularius, Rhodnius prolius* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aondiiella aurantii, Aspidiotus hederae,* Pseudococcus spp. and Psylla spp;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Fieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana*;

from the order of the Coleoptera, for example *Anobium punctatum, Rhizopertha dominica, Bruchidius obtectus, Acanthoescelides obtectus, Hylotrupes bajulus, Agelastica alni, Leptinotarsa decemlineata, Phaedon cochleariae,* Diabrotica spp., *Psylliodes chrysocephala, Epilachna varivestris,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermastes spp., Trogoderma spp., Anthrenus spp., Attagenus spp., Lyctus spp., *Meligethes aenus,* Ptinus spp., *Niptus hololeucus, Gibbium psylloides,* Tribolium spp., *Tenebrio molitor,* Agriotes spp., Conoderus spp., *Melolontha melolntha, Amphimallon solstitialis* and *Costelytra zealandica;* from the order of the Hymenoptera, for example Diprion spp., Hoplacampa spp., Lasius spp., *Monomorium pharaonis* and Vespa spp., from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectis mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The invention is illustrated by the following Examples.

Temperatures are in °C. and refractive indices are measured at 20° C.

EXAMPLE 1

1-(4-ethoxyphenyl)-1-(3-(3-phenoxyphenyl)-2-oxo-propyl)-cyclopropane (Compound 1)

A. 1-cyano-1-(4-ethoxyphenyl)cyclopropane (Compound a)

1.6M n-Butyllithium (680 ml) is added over 5 min to a stirred solution of 4-ethoxyphenyl acetonitrile (56 g) in anhydrous THF (600 ml) at 25° C. under an atmosphere of nitrogen. After 1 h, a solution of 1.2 dichloroethane (111 g) in anhydrous THF (300 ml) is added dropwise over 2 h and the mixture stirred at 25° C. for 16 h. The mixture is then poured onto 3N HCl (1 l), concentrated under reduced pressure, extracted with diethyl ether (x3), washed with water, dried over anhydrous sodium sulphate, the solvent removed under reduced pressure and the residue distilled to give the product, b.p. 116°–120° C., yield 40 g. $n_D$ 1.5320.

B. 1-(4-ethoxyphenyl)-1-cyclopropanemethanal (Compound b)

1M Diisobutylaluminium hydride (14 ml) is added over 3 min. to a stirred solution of 1-cyano-1-(4-ethoxyphenyl)-cyclopropane (1.4 g) in dry benzene (35 ml) and dry n-heptane (14 ml) at 25° C. under an atmosphere of nitrogen. After 3 h the mixture is poured onto 2N H₂SO₄ (100 ml), extracted with diethyl ether (x3), dried and the solvent removed under reduced pressure. Yield 1 g, $n_D$ 1.5272.

C.
1-(ethoxyphenyl)-1-(E/Z-2-methoxyethenyl)-cyclopropane (Compound c)

2.4M Phenyllithium (3.1 ml) is added to a stirred suspension of (methoxymethyl)triphenylphosphonium chloride (2.55 g) in dry diethyl ether (50 ml) at room temperature under an atmosphere of nitrogen. After 30 min a solution of 1-(4-ethoxyphenyl)-1-cyclopropanemethanal (1 g) in diethyl ether (5 ml) is added over 5 min. The mixture is stirred at room temperature overnight, poured onto saturated NH$_4$Cl, extracted with diethyl ether (x3), filtered, dried and the solvent evaporated under reduced pressure. The product is purified by column chromotography on florosil and petroleum ether (b.p. 60°-80° C.) as eluant. Yield 1.6 g, n$_D$ 1.5532.

D. 1-(4-ethoxyphenyl)-1-(2-oxoethyl)-cyclopropane (Compound d)

A solution of 1-(4-ethoxyphenyl)-1-(E/Z-2-methoxyethenyl)-cyclopropane (1.6 g) in THF (5 ml) is added to a mixture of THF (50 ml) and concentrated HCl (6 ml), and stirred at room temperature for 1 h. The mixture is poured onto water, concentrated under reduced pressure, extracted with diethyl ether (x3), washed with water, dried and the solvent evaporated under reduced pressure. Yield 1.2 g n$_D$ 1.5375.

E.
1-(4-ethoxyphenyl)-1-(3-(3-phenoxyphenyl)-2-hydroxypropyl)-cyclopropane (Compound e)

A Grignard reagent prepared from 3-phenoxybenzyl bromide (0.98 g), magnesium turnings (0.1 g) in dry diethyl ether (15 ml) under an atmosphere of nitrogen, is cooled with vigorous stirring to −78° C. To this is added a solution of 1-(4-ethoxyphenyl)-1-(2-oxoethyl)-cyclopropane (0.5 g) in diethyl ether (15 ml) over 5 min. The resulting mixture is allowed to warm up to room temperature over 1 h. Saturated NH$_4$Cl solution is added and the mixture extracted with diethyl ether (x3), dried and the solvent evaporated under reduced pressure. The product is purified by t.l.c. on silica eluted with 10% diethyl ether in petroleum ether (b.p. 60°-80° C.). Yield 0.25 g, n$_D$ 1.5444.

F.
1-(4-ethoxyphenyl)-1-(3-(3-phenoxyphenyl)-2-oxopropyl)-cyclopropane (Compound 1)

Jones reagent (2 ml, prepared by the method described in Fieser and Fieser Vol. 1, p. 142) is added dropwise to a stirring solution of 1-(4-ethoxyphenyl)-1-(3-(3-phenoxyphenyl)-2-hydroxypropyl)-cyclopropane (0.25 g) in acetone (5 ml) whilst maintaining the temperature below 5° C. After 15 min. the mixture is allowed to warm up to room temperature over 4 h, diluted with water, extracted with diethyl ether (x3), washed with water, dried and the solvent evaporated under reduced pressure. The product is purified by thin layer chromatography on silica gel diluted with 15% diethyl ether in petroleum ether (b.p. 60°-80° C.). Yield 0.03 g, n$_D$ 1.5580.

EXAMPLE 2

The following enol ether (f) is prepared as described in Example 1C;
f: 1-(4-chlorophenyl)-1-(E/Z-2-methoxyethenyl)-cyclopropane n$_D$ 1.5806

Compound f is made from 1-(4-chlorophenyl)-cyclopropanemethanal, itself made by oxidation of 1-(4-chlorophenyl)-cyclopropanemethanol with pyridium dichromate, under standard conditions (E. J. Corey and G. Schmidt, Tetrahedron Lett. 1979, 399.)

Enol ether (f) is converted to the corresponding aldehyde (g) by following the method of Example 1D:
g: 1-(4-chlorophenyl)-1-(2-oxethyl)-cyclopropane n$_D$ 1.5816.

The above aldehyde (g) is reacted with a Grignard reagent by following the method of Example 1E to give compound h:
h: 1-(4-chlorophenyl)-1-(3-(3-phenoxyphenyl)-2-hydroxypropyl)-cyclopropane. n$_D$ 1.5325.

Compound h is oxidised to the corresponding ketone (compound 2) by means of pyridinium chlorochromate, the use of which is described in Corey & Suggs, Tetrahedron Lett. 1975, 2647.

Compound 2: 1-(4-chlorophenyl)-1-(3-(3-phenoxyphenyl)-2-oxopropyl)-cyclopropane, n$_D$ 1.5782.

EXAMPLES 3 & 4

The following alcohols (i & j.) are prepared from aldehydes d and g by reaction thereof with a Grignard reagent following procedure 1E:
i. 1-(4-chlorophenyl)-1-(3-(4-fluoro-3-phenoxyphenyl)-2-hydroxypropyl)-cyclopropane n$_D$ 1.5500
j. 1-(4-ethoxyphenyl)-1-(3-(4-fluoro-3-phenoxyphenyl)-2-hydroxypropyl)-cyclopropane n$_D$ 1.5630

Alcohols i & j are oxidised to the corresponding ketones (compounds 3 & 4) by following the procedure described in Examples 2 and 1 respectively:
Compound 3: 1-(4-chlorophenyl)-1-(3-(4-fluoro-3-phenoxyphenyl)-2-oxopropyl)-cyclopropane, n$_D$ 1.5764.
Compound 4: 1-(4-ethoxyphenyl)-1-(3-(4-fluoro-3-phenoxyphenyl)-2-oxopropyl)cyclopropane n$_D$ 1.5580.

Pesticidal activity is assessed against houseflies and mustard beetles by using the following techniques:

Houseflies (*Musca domestica*)

Female flies are treated on the thorax with a one microliter drop of insecticide dissolved in acetone. Two replicates of 15 flies are used at each dose rate and 6 dose rates are used per compound under test. After treatment, the flies are maintained at a temperature of 20°±1° and kill is assessed 24 and 48 hours after treatment. LD$_{50}$ values are calculated in micrograms of insecticide per fly and relative toxicities are calculated from the inverse ratios of the LD$_{50}$ values (see Sawicki et al, Bulletin of the World Health Organisation, 35, 893, (1966) and Sawicki et al, Entomologia and Exp. Appli. 10 253, (1967)).

Mustard beetles (*Phaedon cochleariae* Fab)

Acetone solutions of the test compound are applied ventrally to adult mustard beeltes using a micro drop applicator. The treated insects are maintained for 48 hours after which time kill is assessed. Two replicates of 40 to 50 mustard beetles are used at each dose level and 5 dose levels are used for each compound.

LD$_{50}$ values and thence relative potencies are calculated as for houseflies.

For both insects species relative potencies are calculated by comparison with 5-benzyl-3-furylmethyl (IR)-trans-chrysanthemate (Bioresmethrin) which is one of the more toxic chrysanthemate esters known to houseflies and mustard beetle, its toxicity being about 24 times that of allethrin to houseflies and 65 times that of allethrin to mustard beetles.

Results

Relative potencies to Houseflies and Mustard Beetles (Bioresmethrin=100) are given under HF and MB respectively in the Table.

TABLE

Compounds of formula
$R_A CH_2 COCHDR_B$
(3POB = 3-phenoxybenzyl
4F3POB = 4-fluoro-3-phenoxybenzyl)

| Compound | Ar | $CR_1R_2$ | —$CHDR_B$ | HF | MB |
|---|---|---|---|---|---|
| 1 | 4-ethoxyphenyl | cyclopropyl | 3POB | ca 6 | 3 |
| 2 | 4-chlorophenyl | cyclopropyl | 3POB | 2.1 | 8.7 |
| 3 | 4-chlorophenyl | cyclopropyl | 4F3POB | 9.4 | 33 |
| 4 | 4-ethoxyphenyl | cyclopropyl | 4F3POB | ca 6 | 5.1 |

We claim:

1. A compound of formula I $$R_A CH_2 COCHDR_B \qquad I$$

in which formula:

$R_A$ represents a group $ArCR_1R_2$— in which Ar represents a phenyl or naphthyl group optionally substituted by one or more halogen, alkoxy, haloalkoxy, methylenedioxy or $C_1$–$C_6$ alkyl or haloalkyl groups;

$R_1$ and $R_2$ together with the carbon to which they are attached jointly represent a $C_3$–$C_6$ cycloalkyl group optionally substituted by one or more halogen atoms or $C_1$–$C_6$ cycloalkyl groups and $R_B$ is phenyl, chloro- or fluorophenyl substituted by phenoxy, benzyl or benzoyl and D is hydrogen or cyano.

2. A compound according to claim 1, in which Ar represents substituted or unsubstituted phenyl.

3. A compound according to claim 1, in which Ar represents phenyl substituted at the 3 and/or 4 position.

4. A compound according to claim 1 in which Ar represents phenyl substituted by chlorine or ethoxy.

5. A compound according to claim 1, in which $CR_1R_2$— represents a cyclopropyl.

6. A compound according to claim 1, in which $R_BCHD$ is 3-phenoxybenzyl or 4-fluoro-3-phenoxybenzyl.

7. A pesticidal composition which comprises a compound according to claim 1 of formula I formulated with an inert carrier or diluent.

8. A method of combatting pest infestation in which a pest or a surface or environment susceptible to pest infestation is treated with an effective amount of a compound according to claim 1.

* * * * *